United States Patent [19]

Chiulli

[11] 4,168,701

[45] Sep. 25, 1979

[54] VENOGRAM INJECTOR ASSEMBLY

[76] Inventor: Robert D. Chiulli, 71 Cherry St., Somerville, Mass. 02144

[21] Appl. No.: 874,914

[22] Filed: Feb. 2, 1978

[51] Int. Cl.² .............................................. A61B 6/00
[52] U.S. Cl. ................................ 128/655; 128/218 A
[58] Field of Search ........... 128/218 A, 218 R, 218 P, 128/2 A, 2 R; 222/179

[56] References Cited

U.S. PATENT DOCUMENTS

| 1,736,392 | 11/1929 | Coss et al. | 222/179 |
|---|---|---|---|
| 2,786,468 | 3/1957 | Singer et al. | 128/218 A |
| 3,233,787 | 2/1966 | Ross | 222/179 |
| 3,630,417 | 12/1971 | De Haas | 128/218 A |
| 4,006,736 | 2/1977 | Kranys et al. | 128/2 A |

FOREIGN PATENT DOCUMENTS

| 1116972 | 2/1956 | France | 128/218 A |
| 1295628 | 11/1972 | United Kingdom | 128/218 A |

*Primary Examiner*—Kyle L. Howell
*Attorney, Agent, or Firm*—Scott R. Foster

[57] ABSTRACT

A venogram injector assembly comprising a frame, a holder attached to the frame and adapted to receive and retain a plurality of syringes, a manifold adapted to receive outlet ends of the syringes, a tube adapted for connection at a first end thereof to the manifold and adapted for connection at a second end thereof to a needle for insertion into a vein of a patient, a platen connected to the frame and moveable to engage plunger stems extending from the syringes, and a drive means in communication with the platen, the platen being moveable in response to operation of the drive means to engage the plunger stems, whereby to force fluid in the syringes simultaneously into the manifold and then into the tube, needle, and vein.

10 Claims, 1 Drawing Figure

VENOGRAM INJECTOR ASSEMBLY

BACKGROUND OF THE INVENTION

1. Field of the Invention

This invention relates to venographic devices and is directed more particularly to a venogram injector assembly.

Venography relates to the injection of an aqueous radiopaque solution into a peripheral vein of an extremity accompanied by a series of roentgenograms. A venipuncture is performed on one of the distal small tributaries of the hand or foot and the injection of a suitable amount of the radiopaque solution is made by syringe injection. Under fluoroscopic visualization, the movement of the substance through the venous vasculature may be followed. Roentgenograms are made when optimal filling of the various portions of the pertinent venous anatomy are obtained, thereby recording the anatomy and any pathological changes therein.

2. Description of the Prior Art

In the performance of the aforementioned procedure, it is necessary that a radiologist maintain a continuous flow of the radiopaque solution to insure complete venous filling and to minimize dilution of the injected solution by the nonradiopaque blood which continues to flow within the veins. The amount of substance required usually necessitates the use of a plurality of syringes. During an exchange of syringes, the radiopacity of the solution becomes attenuated as it is displaced by the influx of blood. Further, in the haste to exchange syringes, an air bubble is sometimes introduced and can simulate venous thrombosis if it lodges within one of the veins under scrutiny.

Simultaneously with the injection and exchange of syringes, the radiologist must control a fluoroscopy unit and make the appropriate exposures. Thus, the radiologist has in the past generally had one hand occupied with a syringe in an attempt to maintain a continuous injection and the other hand occupied with the fluoroscope in order to study and film the venous anatomy.

SUMMARY OF THE INVENTION

An object of the present invention is to provide a venogram injector assembly which facilitates injection of the needed quantity of radiopaque solution in continuous and rapid fashion without hand operation.

A further object of the invention is to provide such a device as is reliable in operation and easy to use, yet relatively non-complex and therefore inexpensive to manufacture.

With the above and other objects in view, as will hereinafter appear, a feature of the present invention is the provision of a venogram injector assembly comprising a frame, holder means attached to the frame and adapted to receive and retain syringe means, a manifold adapted to receive an outlet end of the syringe means, a tube adapted for connection at a first end thereof to the manifold and adapted for connection at a second end thereof to an intravenous needle, platen means connected to the frame and moveable to engage plunger stem means extending from the syringe means, and a drive means in communication with the platen means, the platen means being moveable in response to operation of the drive means to engage the stem means, whereby to force fluid in the syringe means into the manifold and thence into the tube, needle and vein.

In accordance with a further feature of the invention, the syringe means comprises a plurality of syringe barrels having the plunger stem means extending therefrom, the platen means being operative to engage the plunger stem means of each of the syringe barrels simultaneously, the manifold being adapted to receive the outlet ends of the syringe barrels.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

DESCRIPTION OF THE DRAWINGS

Reference is made to the accompanying drawing in which is shown an illustrative embodiment of the invention from which its novel features and advantages will be apparent.

DESCRIPTION OF THE PREFERRED EMBODIMENT

Figure 1:
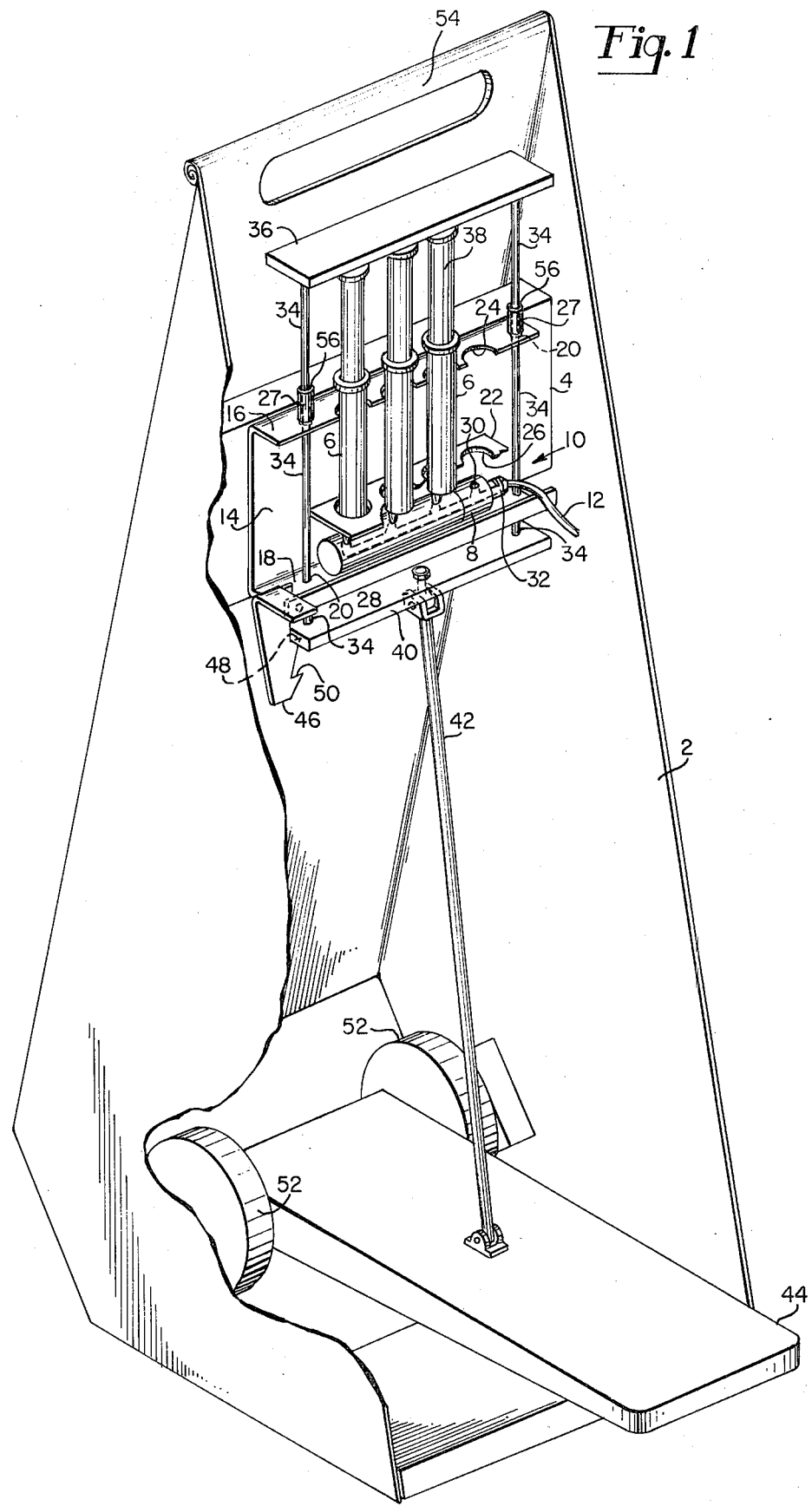
FIG. 1 is a perspective view of one form of venogram injector assembly illustrative of an embodiment of the invention.

Referring to the drawings, it will be seen that the illustrative embodiment includes a frame 2 having mounted thereon a holder 4 adapted to receive and retain syringes 6. The holder 4 is further adapted to receive and retain a manifold 8 which in turn is adapted to receive discharge ends of the syringes 6. A first end 10 of a tube 12 is adapted to be connected to the manifold 8, the tube 12 having a second end (not shown) which is adapted for connection onto a needle adapted for insertion intravenously into a vein of an extremity of a patient.

The holder 4 may include a back plate 14 having an upper flange 16 extending from an upper portion thereof and a lower flange 18 extending from a lower portion thereof. Aligned holes 20 are located in the flanges 16, 18. The upper flange and a shelf member 22 extending from the backplate 14 have, respectively, recesses 24 and holes 26 therein so aligned as to receive the aforementioned syringes 6.

The upper flange 16 is provided with collars 27 aligned with the holes 20 and extending upwardly therefrom.

The lower flange 18 is provided with a face plate 28, which, in conjunction with the backplate 14 and the lower flange 18, provides a trough for the reception of the manifold 8.

The manifold 8 comprises a disposable cannister having holes 30 therein for reception of the discharge ends of the syringes. At one end, the manifold is provided with a connector means 32 by which the manifold may be quickly connected and disconnected to and from the tube 12.

Disposed in the aligned holes 20 are rods 34 interconnected at their upper ends by a platen 36 which is aligned with and engageable with plunger stem means 38 extending from the syringes 6.

The lower ends of the rods 34 are interconnected by a crossmember 40 which in turn is pivotally attached to an actuator rod 42. Thus, movement of the actuator rod 42 causes movement of the crossmember 40, the rods 34, and the platen 36, all as one unit.

A drive means is connected to the rod 42 so that an operator may cause the rod to move downwardly. The drive means may comprise a motorized moving means or may, as shown, comprise a manually moveable means, such as a lever, and preferably a foot-actuated lever, a foot pedal 44, connected to the frame 2.

The holder 4 is preferably provided with a pivotally mounted tab 46 having upper and lower ratchet surfaces 48, 50. The ratchet surfaces are so arranged that when the crossmember 40 rests upon the upper ratchet surface 48, the platen is sufficiently elevated to permit easy removal and replacement of the syringes 6. When the crossmember 40 rests upon the lower ratchet surface 50, the platen is engaged with the free ends of the plunger stems 38.

In the embodiment illustrated, the frame 2 is provided with wheels 52 and handle means 54 by which the whole assembly may be transported to a fluoroscopic table location and brought into use. If preferred, however, the assembly may be a generally permanent installation.

In use, a disposable-type manifold 8 is connected to the first end of the tube 12 and inserted in the holder 4. The crossmember 40 is placed on the upper ratchet surface 48 of the tab 46 by manually lifting the entire slide assembly to its uppermost position. A plurality of the syringes 6 filled with radiopaque solution are then introduced into the holes 30, 26 and recesses 24, as shown in the drawing, the stems 38 being fully extended. The tab 46 is then pivoted outwardly to allow the bar 40 to descend to the lower ratchet surface 50. In so doing, the pusher member 36 engages the stem means 38 and causes a sufficient discharge of solution from the syringes to fill the manifold 8 and the tube 12, expelling the air from the manifold and tube. The second end of the tube is then connected onto the intravenous needle. The tab 46 is then removed from the bar 40 and the descent of the pusher member 36 is controlled by the operation of the foot pedal 44 by the operator, leaving the hands of the operator free for control of the fluoroscopy unit used in the venography procedure.

The platen 36 descends in accordance with the force applied to the foot pedal 44, or other drive means, until the platen strikes the upper ends 56 of the collars 27 which project above the upper flange 16 and act as stops. The collars 27 are of a height sufficient to limit the downward travel of the platen such that a preset amount of solution is retained in each syringe, usually about 5 cubic centimeters. The collars 27 thus prevent the discharge of the last five or so cubic centimeters of solution from each syringe, whereby to eliminate the possibility of inadvertent intravenous administration of air which may not have been entirely cleared from the syringes.

It is to be understood that the present invention is by no means limited to the particular construction herein disclosed and/or shown in the drawings, but also comprises any modifications or equivalents within the scope of the disclosure.

Having thus described my invention, which I claim as new and desire to secure by Letters Patent of the United States is:

1. A venogram injector assembly comprising a frame, holder means fixed to said frame and adapted to receive and retain a plurality of syringes, a manifold for disposition in said holder means and adapted to receive outlet ends of said syringes, a tube adapted for connection at a first end thereof to said manifold, a platen mounted on said assembly and movable to engage simultaneously plunger stems extending from said syringes, and drive means in communication with said platen, said platen being movable in response to operation of said drive means to engage said stems, whereby to force fluid in said syringes into said manifold and thence into said tube.

2. The invention in accordance with claim 1 in which said manifold comprises an elongated cannister having holes therein along a side thereof for reception of said outlet ends of said syringes and having connector means at one end thereof for connection to said tube.

3. The invention in accordance with claim 2 in which said holder means comprises a lower flange adapted to receive said manifold and an upper flange having recesses therein for receiving said syringes in an attitude generally normal to said manifold.

4. The invention in accordance with claim 3 in which said holder means includes a shelf disposed between said upper and lower flanges and having holes therein adapted to receive and retain said syringes.

5. The invention in accordance with claim 3 in which said platen is fixed to rod means slidably disposed in said holder means and connected to said drive means.

6. The invention in accordance with claim 5 including stop means mounted on said holder means, said stop means being operative to limit movement of said platen to prevent complete emptying of said syringes.

7. The invention in accordance with claim 6 in which said stop means comprise collar members disposed around said rod means.

8. The invention in accordance with claim 7 in which said rod means are slidably disposed in aligned holes in said upper and lower flanges, and said collar members are fixed to said upper flange.

9. The invention in accordance with claim 8 in which said rod means at ends remote from said platen are fixed to a crossmember which is connected to an actuator rod, said actuator rod being in communication with said drive means.

10. The invention in accordance with claim 9 including a tab member pivotally connected to said holder means and having a ratchet surface engageable with said crossmember to fix and hold said platen at a predetermined position.

* * * * *